United States Patent
Cow et al.

(10) Patent No.: US 10,660,846 B2
(45) Date of Patent: May 26, 2020

(54) METHOD AND COMPOSITION FOR LIGHTENING SKIN USING A CELL CULTURE EXTRACT

(71) Applicant: Johnson & Johnson Consumer Inc., Skillman, NJ (US)

(72) Inventors: Bee Khim Cow, Singapore (SG); Chong Jin Loy, Singapore (SG); Thidarat Nimchua, Pathum Thani (TH); Juthamas Suwanprateep, Pathum Thani (TH)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/761,515

(22) PCT Filed: Sep. 28, 2016

(86) PCT No.: PCT/US2016/054060
§ 371 (c)(1),
(2) Date: Mar. 20, 2018

(87) PCT Pub. No.: WO2017/058840
PCT Pub. Date: Apr. 6, 2017

(65) Prior Publication Data
US 2018/0243205 A1 Aug. 30, 2018

Related U.S. Application Data

(60) Provisional application No. 62/234,232, filed on Sep. 29, 2015, provisional application No. 62/234,239, filed on Sep. 29, 2015, provisional application No. 62/234,247, filed on Sep. 29, 2015.

(51) Int. Cl.
| | | |
|---|---|---|
| *A61K 8/9728* | (2017.01) | |
| *A61K 8/02* | (2006.01) | |
| *A61Q 19/02* | (2006.01) | |
| *A61K 8/9706* | (2017.01) | |
| *C12N 1/14* | (2006.01) | |

(52) U.S. Cl.
CPC ......... *A61K 8/9728* (2017.08); *A61K 8/0208* (2013.01); *A61K 8/0212* (2013.01); *A61K 8/9706* (2017.08); *A61Q 19/02* (2013.01); *C12N 1/14* (2013.01); *C12N 2500/30* (2013.01)

(58) Field of Classification Search
None
See application file for complete search history.

(56) References Cited

U.S. PATENT DOCUMENTS

| | | |
|---|---|---|
| 5,578,296 A | 11/1996 | Kashino et al. |
| 6,514,506 B1 | 2/2003 | Mammone et al. |
| 7,291,340 B2 | 11/2007 | Mammone et al. |
| 7,452,547 B2 | 11/2008 | Lambino et al. |
| 8,691,194 B2 | 4/2014 | Belinky et al. |
| 8,956,624 B2 | 2/2015 | Schnittger et al. |
| 2006/0141014 A1 | 6/2006 | Eknoian et al. |
| 2007/0196523 A1 | 8/2007 | Koganov |
| 2009/0241242 A1 | 10/2009 | Beatty et al. |
| 2012/0045490 A1 | 2/2012 | Kaur et al. |
| 2012/0045491 A1 | 2/2012 | Loy et al. |
| 2012/0045530 A1 | 2/2012 | Kaur et al. |

FOREIGN PATENT DOCUMENTS

| | | |
|---|---|---|
| DE | 102009045798 | * 10/2009 |
| JP | 2005194214 A | 7/2005 |

OTHER PUBLICATIONS

Guerra et al. "Production of laccase and manganese peroxidase by white-rot fungi from sugarcane bagasse in solid bed: Use for dyes decolourisation" 2008.*
Butler et al. "Destruction of Fungal Melanins by Ligninases of Phanerochaete chyrososporium and Other White Rot Fungi" 1998 abstract.*
Wu, "Cultural Studies of Four Polypores (Basidiomycotina) Collected From Taiwan", Bulletin of National Museum of Natural Science 1996 8:65-72.
U.S. Appl. No. 62/234,232, filed Sep. 29, 2015, Cow et al.
U.S. Appl. No. 62/234,239, filed Sep. 29, 2015, Cow et al.
U.S. Appl. No. 62/234,247, filed Sep. 29, 2015, Cow et al.
Ando et al., "Qusai-Drugs Developed in Japan for the Prevention or Treatment of Hyperpigmentary Disorders", *International Journal of Molecular Sciences* (2010) 11:2566-2575.
Berrin et al., "Exploring the Natural Fungal Biodiversity of Tropical and Temperate Forests toward Improvement of Biomass Conversion", Applied and Environmental Microbiology, American Society for Microbiology, US, vol. 78, No. 18, Sep. 1, 2012, pp. 6483-6490 (XP008160296).
Guerra et al., "Production of laccase and manganese peroxidase by white-rot fungi from sugarcane bagasse in solid bed: Use for dyes decolourisation",*Sugar Technology*, Oct. 1, 2008, 10(3):260-264).
Lyra et al., "Decolorization of synthetic dyes by basidiomycetes isolated from woods of the Atlantic Forest (PE), Brazil", World Journal of Microbiology and Biotechnology, Kluwer Academic Publishers, DO, vol. 25, No. 8, Apr. 10, 2009, pp. 1499-1504, (XP019734623).
Oldenhove De Guertechin, Chapter 37, Classification of surfactants, pp. 431-450, in the Handbook of Cosmetic Science and Technology, edited by Barel et al., Published in 2001 by Marcel Dekker, Inc., New York, NY.

(Continued)

*Primary Examiner* — Robert A Wax
*Assistant Examiner* — Danah Al-Awadi
(74) *Attorney, Agent, or Firm* — Michelle Cristaldi

(57) ABSTRACT

A composition and method for lightening skin includes applying a skin care composition including cell culture extract of *Earliella scabrosa*. A method for culturing *Earliella scabrosa* including using an inducer, select carbohydrates and optimal processing condition produces increased skin lightening properties of the cell culture extract.

27 Claims, 3 Drawing Sheets

(56) References Cited

OTHER PUBLICATIONS

Peng et al., "Antifungal Activity of In-vitro Grown Earliella Scabrosa, a Malaysian Fungus on Selected Wood-degrading Fungi of Rubberwood", Journal of Physical Science, Jul. 1, 2013, pp. 21-33. Retrieved from the Internet: URL:http://web.usm.my/jps/24-2-13/24-2-2.pdf <retrieved on Nov. 10, 2016> (XP055318357).
Solano et al., "Hypopigmenting agents: an updated review on Biological, chemical and clinical aspects", *Pigment Cell Res*. (2006) 19:550-571.
Colipa Guidelines: Guideline for the Colorimetric Determination of Skin Colour Typing and Prediction of the Minimal Erythema! Dose (Med) Without UV Exposure, responsible editor S. Marx, published in 2007.
Zocchi, Chapter 35, Skin Feel Agents, pp. 399-415, in the Handbook of Cosmetic Science and Technology, edited by Barel et al., Published in 2001 by Marcel Dekker, Inc., New York, NY.
International search report dated Nov. 29, 2016, for international application PCT/US2016/054060.

\* cited by examiner

METHOD AND COMPOSITION FOR LIGHTENING SKIN USING A CELL CULTURE EXTRACT

CROSS-REFERENCE TO RELATED APPLICATIONS

This application is the national stage entry of international application PCT/US2016/54060 filed on Sep. 28, 2016 which claims benefit of U.S. Provisional Application 62/234,232, filed Sep. 29, 2015; U.S. Provisional Application 62/234,239; filed Sep. 29, 2015; and U.S. Provisional Application 62/234,247, filed Sep. 29, 2015. The complete disclosures of the aforementioned patent applications are hereby incorporated herein by reference for all purposes.

FIELD OF THE INVENTION

The present invention relates to topical compositions for improving the appearance of skin including lightening of the skin using an effective amount of a cell culture extract of *Earliella scabrosa*.

BACKGROUND OF THE INVENTION

Modifying skin surface melanin is important because more than 50% of melanin is located in the outer layers of skin, especially after UV exposure. Melanin that is being made by melanocytes is transferred from melanocytes to keratinocytes and it contributed to the color of skin being perceived from the surface. By modifying the optical properties of skin surface melanin, it can modify the appearance of skin color, offer faster lightening of skin tone and even out variations in skin tone.

It is known that fungi and bacteria can attack and liquefy low rank coal (also known as brown coal or lignite). These micro-organisms can utilize coal as their growth substrate when they use it as their carbon source, which lead to the degradation of coal via secretion of enzymes like peroxidases, metabolite and natural chelators that remove complex-forming metal ions from the coal structure. Part of the coal composition is fossilized remains of plants that contain mostly lignin, a complex polymer that makes up the cell wall of plants which helps give wood its strength and rigidity.

*Earliella* is a genus of wood degrading macrofungi in the family Polyporaceae. This is a monotypic genus, containing the single species *Earliella scabrosa*. It is fairly common in tropical and subtropical regions, and grows on dead wood of various angiosperms. This species is variable in characteristics and therefore encompass several synonyms (Sheng-Hua Wu, "Cultural Studies of Four Polypores (Basidiomycotina) Collected in Taiwan", Bulletine of National Museum of Natural Science, No. 8, pp. 65-72, 1996)

U.S. Pat. No. 8,956,624 discloses compositions and methods for treating skin with extract from Trametes veriscolor. U.S. Pat. No. 8,691,194 discloses methods of producing lignin peroxidase derived from *Phanerochaete chrysosporium* and its use in skin and hair lightening. U.S. Pat. No. 7,291,340 discloses melanin degrading extract derived from *Exophiala monsonii*. U.S. Pat. No. 6,514,506 teaches whitening compositions containing enzyme from *Aspergillus fumigatus*. U.S. Pat. No. 5,578,296 discloses decomposition of melanin using a culture of *Basidiomycetes*.

There are several commercially available cosmetic products that have been sold in the United States for correcting spots that include fungus or yeast extracts. These products include Lacome Blanc Expert Melanolyser III™ Integral Whiteness Spot Eraser, Clinique Derma White Clinical Brightening Essence and Estee Lauder Cyberwhite EX Advanced Performance Brightening Essence.

The present invention is related to the discovery that a class of white rot fungi, *Earliella scabrosa*, can secrete melanolytic enzymes. These enzymes can be incorporated into skin care compositions used for skin lightening. Additionally, the invention is directed to a method for culturing the fungi to maximize the skin lightening properties of the culture.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

All percentages listed herein, unless otherwise stated, are weight percentages based on the total weight of the composition.

SUMMARY OF THE INVENTION

The present invention is directed to a method of lightening the skin by applying to human skin in need of lightening a composition including a cosmetically acceptable carrier and a skin lightening effective amount of a cell culture extract of *Earliella scabrosa*. The human skin in need of skin lightening can include skin darkened by UV, skin with uneven skin tone, skin having one or more pigmented spots, melanin spots, age spots, sun spots, senile lentigos, freckles, lentigos simplex, pigmented solar keratosis, seborrhoeic keratosis, melasma, acne marks, and combinations. The composition used in the method can include about 0.0001% to about 40% or 0.01% to about 25% or from about 0.1% to about 10% by weight of the cell culture extract of *Earliella scabrosa*. The composition used in the method can be in the form of a solution, suspension, lotion, cream, serum, gel, stick, spray, ointment, liquid wash, soap bar, shampoo, hair conditioner, paste, foam, powder, mousse, shaving cream, hydrogel, or film-forming product.

The step of applying the composition to the skin can include transferring the composition from a substrate to the skin. The substrate can be a wipe or facial mask. The composition used in the method can include an additional skin lightening active agent. The method of applying the composition to the skin can include applying the composition with a cell culture extract of *Earliella scabrosa* once or twice daily. The compositions used can be two or more different compositions comprising a cell culture extract of *Earliella scabrosa*. The two or more different compositions can independently be lotions, cleansers, masks, essence, wipes, creams, serums and gels.

The cell culture extract used in the present method can have a melanin degrading activity of from about 500 to about 2000 U/ml or from about 600 to about 1800 U/ml or from about 1000 to about 1800 U/ml.

Another aspect of the present invention includes a method of culturing *Earliella scabrosa* in an aqueous liquid culture medium including the steps of inoculating a liquid culture medium with *Earliella scabrosa* and admixing the liquid culture medium with an inducer in an amount from about 10 g/ml to about 2000 g/ml. The inducer can include synthetic melanin, sepia melanin, 3,4-dimethoxybenzyl alcohol, lignin, Benzyl alcohol, cinnamic acid, guaiacol, methyl salicylate, benzenediol, benzoquinone, Gallic acid, salicylic acid, eugenol, caffeic acid, xylenol and mixtures thereof. The inducer can be used in an amount from about 30 mg/ml to about 1000 mg/ml, or from about 200 mg/ml to about 400 mg/ml or from about 245 mg/ml to about 350 mg/ml.

The method of culturing can also include the step of maintaining the pH of the liquid culture medium between about 5 to about 6. Additionally, the method of culturing can include adding a nitrogen source to the liquid culture medium. The nitrogen source can be selected from the group consisting of rice bran, wheat bran, ammonium nitrate, yeast extract or mixtures thereof. The nitrogen source is added to the culture medium in an amount from about 0.1 g/L to about 25 g/L or from about 0.2 g/l to about 20 g/L or from about 5 g/L to about 20 g/L.

The method of culturing can also include the step of agitating the liquid culture medium at a rate of about 100 rpm with an incubator shaker. The method can also include adding a carbon source to the liquid culture medium. The carbon source can be glucose, dextrose or mixtures thereof. The amount of the carbon source added to the liquid culture medium is from about 2.0 g/L to about 20 g/L or from about 5.0 g/L to about 15 g/L or from about 5 g/L to about 10 g/L. The method of culturing can including the step of filtering the liquid culture media with a mesh screen.

Another aspect of the invention is a skin care composition including a cosmetically acceptable carrier and a cell culture extract of *Earliella scabrosa* in an amount effective to lighten human skin. The composition can include from about 0.0001% to about 40% or about from about 0.01% to about 25 or from about 0.1% to about 10% by weight of the cell culture extract of *Earliella scabrosa*. The skin care composition can include a second skin lightening agent.

DETAILED DESCRIPTION OF THE INVENTION

Cell Culture Extract

Figure 1:
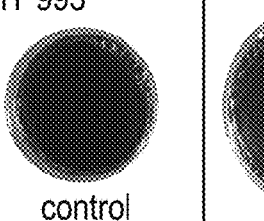
FIG. 1 is a photograph of a series of melanin agar plates cultured with the MY993 strain of *Earliella scabrosa* showing the effect of decolorizing melanin.

As used herein, "cell culture extract" means the material produced from a cell culture of a microorganism after the cell culturing process. The extract can be made from a liquid media that is centrifuged. The supernatant is then filtered. The material that passes through the filter is the cell culture extract. This is also known as a cell culture filtrate.

The present invention is directed to a cell culture extract produced by culturing fungi. More particularly, the cell culture extract is made from a culture of *Earliella scabrosa*. Even more particularly, the cell culture extract is made from a culture of *Earliella scabrosa* MY993 or MY261. The fungal strains MY993 and MY261 were found in Thailand and were isolated firstly by researchers from national center for genetic engineering and biotechnology (BIOTEC) in 2006. Consequently, both fungi were identified as *Earliella scabrosa* by morphological-based methods and were subsequently deposited at Thailand Bioresource Research Center (TBRC), Thailand Science Park, Phaholyothin Road, Klong 1, Klongluang, Pathumthani 12120, Thailand with designated TBRC no. 2014 and 2015, respectively. The fungal strains MY993 (TRBC 2014) and MY261 (TBRC 2015) were deposited under the Budapest treaty with Deutsche Sammlung von Mikroorganismen und Zellkulturen GmbH (DSMZ) Germany on Aug. 18, 2016 and given numbers DSM 32358 and DSM 32359, respectively.

The cell culture extracts according to the present invention have a melanin degrading activity of from about 500 to about 2000 U/ml, more particularly from about 600 to about 1800 U/ml and even more particularly from about 1000 to about 1750 U/ml. U/ml means unit of melanin degrading enzyme per ml of extract as described in the melanin degrading assay detailed in Example 3.

Method of Skin Lightening

The present invention is directed to a method of lightening skin by applying to the skin in need of lightening a composition comprising a cell culture extract of certain fungi. More particularly, the present invention is directed to a method of lightening skin by applying to the skin in need of lightening a composition including a cell culture extract of *Earliella scabrosa*.

As used herein, the term "lightening the skin" refers generally to lightening, brightening, whitening, and/or evening of the skin tone, skin color, and/or shade of skin, and/or to the reduction in sallowness, and/or to the lightening and/or fading of hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In certain embodiments, "lightening the skin" also refers to increased skin radiance, glow, translucency and/or luminescence and/or obtaining a more radiant, glowing, translucent or luminous skin tone appearance or a less yellow or sallow skin tone. In certain preferred embodiments, "lightening the skin" refers to lightening and evening the skin tone, increasing skin radiance and/or lightening age spots.

As used herein, the term "skin in need of skin lightening treatment" refers generally to skin that exhibits one or more property selected from the group consisting of: skin having a measured Individual Typology Angle (ITA) value below 41 as determined per the Colipa Guideline: Guideline For The Colorimetric Determination Of Skin Colour Typing And Prediction Of The Minimal Erythemal Dose (Med) Without Uv Exposure published in 2007, which is incorporated herein by reference and further described below, darkened and/or sallow skin, including skin darkened by UV, skin with uneven skin tone, or skin with one or more hyperpigmented marks and/or lesions including, but not limited to, pigmented spots, melanin spots, age spots, sun spots, senile lentigos, freckles, lentigos simplex, pigmented solar keratosis, seborrhoeic keratosis, melasma, acne marks, post-inflammatory hyperpigmentation, lentigines, ephelides, combinations of two or more thereof and the like. In the COLIPA guidelines, skin color is defined function of the ITA value as: very light skin >55; Light skin 41-55, Intermediate 28-41, and Tan skin <28. In certain preferred embodiments, "skin in need of skin lightening" refers to individuals with a skin having an ITA value of less than 41, such as about 40 or less, about 35 or less, about 30 or less, or more preferably about 28 or less. In certain other preferred embodiments, the present invention is directed to compositions and methods for use on skin in need of skin lightening treatment selected from sallow and/or darkened skin. In certain other preferred embodiments, the present invention is directed to compositions and methods for use on skin in need of skin lightening treatment selected from the group consisting of age spots, freckles, marks left after acne, and combinations of two or more thereof. As used herein, "skin in need of improving the signs of aging" means a skin that is, but not limited to, sagging, loose, lax, rough, wrinkly, thinned, and uneven. Improving the signs of aging means improving the firmness of the skin, improving the texture of the skin, improving the appearance of wrinkles in skin, improving the skin tone or the treatment of external aggressions in skin.

As used herein, "improving the skin tone" means the lightening of the appearance of the skin (e.g., lightening pigmented marks or lesions, reducing skin sallowness, and/or evening the color of the skin).

As used herein, "cosmetically/dermatologically acceptable" means suitable for use in contact with tissues (e.g., the skin or hair) without undue toxicity, incompatibility, instability, irritation, allergic response, and the like.

As used herein, a "safe and effective amount" means an amount of the extract or of the composition sufficient to induce the desired effect, but low enough to avoid serious side effects, including cytotoxicity and the like. The safe and effective amount of the compound, extract, or composition will vary with, e.g., the age, health and environmental exposure of the end user, the duration and nature of the treatment, the specific extract, ingredient, or composition employed, the particular pharmaceutically-acceptable carrier utilized, and like factors.

The safe and effective amount of the compound, extract, or composition will vary with, e.g., the age, health and environmental exposure of the end user, the duration and nature of the treatment, the specific extract, ingredient, or composition employed, the particular pharmaceutically-acceptable carrier utilized, and like factors.

For embodiments comprising skin lightening uses of the composition, a "skin lightening effective amount" means an amount of extract that is effective to achieve a ΔL value that is greater than zero in the Skin Epidermal Equivalents Model as a skin Lightening Test (ΔL) as described below. In certain preferred embodiments, the skin lightening effective amount is an amount effective to achieve a ΔL value of about 1 or greater.

The amount of the cell culture extract in the skin care composition used in the method of lightening skin will vary from about 0.001 to about 40 weight percent of the skin care composition. More particularly, the amount will be from about 0.01 to about 25 weight percent of the skin care composition. Even more particularly, amount will be from the about 0.1 to about 10 weight percent of the skin care composition.

Skin Care Compositions

The present invention is directed to a skin care composition containing an *Earliella scabrosa* cell culture extract and a carrier. The *Earliella scabrosa* cell culture extract is present in the skin care composition in an amount sufficient to lighten skin. Any suitable carrier may be used in the skin care compositions according to the present invention. Preferably, the carrier is a cosmetically-acceptable carrier. As will be recognized by those of skill in the art, cosmetically acceptable carriers comprise carriers that are suitable for use in contact with the body, in particular the skin, without undue toxicity, incompatibility, instability, irritation, allergic response, and the like. A safe and effective amount of carrier is from about 50% to about 99.999%, preferably from about 80% to about 99.9%, more preferably from about 99.9% to about 95%, most preferably from about 98% to about 99.8% by weight of the composition.

The carrier can be in a wide variety of forms. For example, carriers in the form of emulsions, including, but not limited to, oil-in-water, water-in-oil, water-in-oil-in-water, and oil-in-water-in-silicone emulsions, are useful herein. These emulsions can cover a broad range of viscosities, e.g., from about 100 cps to about 200,000 cps Examples of suitable cosmetically acceptable carriers include cosmetically acceptable solvents and materials for cosmetic solutions, suspensions, lotions, creams, serums, essences, gels, toners, sticks, sprays, ointments, liquid washes and soap bars, shampoos, hair conditioners, pastes, foams, mousses, powders, shaving creams, wipes, patches, strips, powered patches, micro-needle patches, bandages, hydrogels, film-forming products, facial and skin masks, make-up, liquid drops, cosmetic films and the like. These product types may contain several types of cosmetically-acceptable carriers including, but not limited to solutions, suspensions, emulsions such as micro-emulsions and nano-emulsions, gels, solids, liposomes, other encapsulation technologies and the like.

The following are non-limiting examples of carriers. Other carriers can be formulated by those of ordinary skill in the art. In one embodiment, the carrier contains water. In a further embodiment, the carrier may also contain one or more aqueous or organic solvents. Examples of organic solvents include, but are not limited to: dimethyl isosorbide; isopropylmyristate; surfactants of cationic, anionic and non-ionic nature; vegetable oils; mineral oils; waxes; gums; synthetic and natural gelling agents; alkanols; glycols; and polyols. Examples of glycols include, but are not limited to, glycerin, propylene glycol, butylene glycol, pentalene glycol, hexylene glycol, polyethylene glycol, polypropylene glycol, diethylene glycol, triethylene glycol, capryl glycol, glycerol, butanediol and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol. The organic solvents may be present in the carrier in an amount, based upon the total weight of the carrier, of from about 1 percent to about 99.99 percent (e.g., from about 20 percent to about 50 percent). Water may be present in the carrier (prior to use) in an amount, based upon the total weight of the carrier, of from about 5 percent to about 95 percent (e.g., from about 50 percent to about 90 percent). Solutions may contain any suitable amounts of solvent, including from about 40 to about 99.99%. Certain preferred solutions contain from about 50 to about 99.9%, from about 60 to about 99%, from about 70 to about 99%, from about 80 to about 99%, or from about 90 to 99% of solvent.

A lotion can be made from such a solution. Lotions typically contain at least one emollient in addition to a solvent. Lotions may comprise from about 1% to about 20%

(e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s).

The compositions useful in the present invention can also be formulated as emulsions. If the carrier is an emulsion, from about 1% to about 10% (e.g., from about 2% to about 5%) of the carrier contains an emulsifier(s). Emulsifiers may be nonionic, anionic or cationic.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type, and water-in-oil type are well-known in the art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers, and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The compositions of the present invention can also be formulated into a solid formulation (e.g., a wax-based stick, soap bar composition, powder, or wipe). The composition of the present invention can also be combined with a solid, semi-solid, or dissolvable substrate (e.g., a wipe, mask, pad, glove, or strip).

The compositions of the present invention may further comprise any of a variety of additional cosmetically active agents. Examples of suitable additional active agents include: skin lightening agents, darkening agents, additional anti-aging agents, tropoelastin promoters, collagen promoters, anti-acne agents, shine control agents, anti-microbial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, odor-control agents such as odor masking or pH changing agents, and the like.

Examples of various suitable additional cosmetically acceptable actives include hydroxy acids; benzoyl peroxide; D-panthenol; UV filters such as but not limited to avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate 0 (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide; carotenoids; free radical scavengers; spin traps; retinoids and retinoid precursors such as 30 retinol, retinoic acid and retinyl palmitate; ceramides; polyunsaturated fatty acids; essential fatty acids; enzymes; enzyme inhibitors; enzyme mediators such as 2,2-azinobis (3-ethylbenzothiazoline-6-sulfonate) diammonium salt (ARTS) and vanillin; minerals; hormones such as estrogens; steroids such as hydrocortisone; 2-dimethylaminoethanol; copper salts such as copper chloride; peptides containing copper such as Cu:Gly-His-Lys, coenzyme Q10; amino acids such a proline; vitamins; lactobionic acid; acetyl-coenzyme A; niacin; riboflavin; thiamin; ribose; electron transporters such as NADH and FADH2; and other botanical extracts such as oat, aloe vera, Feverfew, Soy, Shiitake mushroom extracts, and derivatives and mixtures thereof.

In certain preferred embodiments, the skin care compositions comprise cell culture extracts of *Earliella scabrosa* and at least one additional skin moisturizing active agent. Examples of additional skin moisturizing agents include glycerin, propylene glycol, butylene glycol, pentalene glycol, hexylene glycol, polyethylene glycol, polypropylene glycol, diethylene glycol, triethylene glycol, capryl glycol, glycerol, butanediol and hexanetriol, or mixtures thereof.

In certain preferred embodiments, the compositions of the present invention are skin care compositions that comprise cell culture extracts of *Earliella scabrosa* and at least one additional agent for improving the signs of aging. Examples of suitable additional agents improving the signs of aging include, but are not limited to, tropoelastin promoters, collagen promoters, retinoids, hyaluronic acid, dimethylaminoethanol, N,N,N',N'-Tetrakis(2-hydroxypropyl)ethylenediamine, alpha hydrox acids, polyhydroxyacids, and combinations of two or more thereof.

"Tropoelastin promoters," as used herein, refers to a class of compounds that possess the biological activity of enhancing the production of tropoelastin. Tropoelastin promoters, according to the present invention, include all natural or synthetic compounds that are capable of enhancing the production of tropoelastin in the human body.

Examples of suitable tropoelastin promoters include, but are not limited to, blackberry extracts, cotinus extracts, feverfew extracts, extracts of *Phyllanthus niruri* and bimetal complexes having copper and/or zinc constituents. The bimetal complex having copper and/or zinc constituents may be, for example, copper-zinc citrate, copper-zinc oxalate, copperzinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof. In a preferred embodiment, the tropoelastin promoter is selected from blackberry extracts, cotinus extracts, feverfew extracts, and combinations thereof. In a particularly preferred embodiment, the tropoelastin promoter is selected from blackberry extracts, feverfew extracts, and combinations thereof.

By "cotinus extract," it is meant an extract of the leaves of "*Cotinus coggygria*," such as a water extract thereof, available from Bilkokoop of Sofia, Bulgaria.

By "blackberry extract," it is meant a blend of compounds isolated from the plant of the genus *Rubus*, and preferably *Rubus fruticosus*. In one embodiment, the compounds are isolated from the flowers of the plant. In a further embodiment, the compounds are isolated from dried flowers of the plant. Such compounds may be isolated from one or more part of the plant (e.g., the whole plant, flower, seed, root, rhizome, stem, fruit and/or leaf of the plant). In a preferred embodiment, the blackberry extract is a blackberry leaf extract. One particularly suitable blackberry extract is produced by extracting the leaves of *Rubus fruticosus* with a mixture of water and ethanol compounded to an activity of about 5% to about 10%, with a maltodextrin matrix, commercially available from Symrise Inc. of Teterboro, N.J., and is sold under the name "SymMatrix."

Extracts of "*Phyllanthus niruri*" may be harvested and used as the whole plant, or optionally one or more parts of the plant (e.g., flower, seed, root, rhizome, stem, fruit and/or leaf of the plant) may be used. The *Phyllanthus niruri* plant or parts thereof may be finely divided, such as by grinding or milling, to a powder. A suitable milled form of *Phyllanthus niruri* is commercially available from Raintree Nutrition, Inc., of Carson City, Nev. Preferably, a low molecular weight fraction of *Phyllanthus niruri* is used, for instance a fraction of *Phyllanthus niruri* substantially free of molecular species having a molecular weight of greater than about 100,000 daltons. Preferably, such low molecular weight fraction is water extractable from the *Phyllanthus niruri* plant.

Compositions of the present invention may include a cosmetically effective amount of one or more tropoelastin promoters such as those described above. The compositions preferably include, on an active basis, from about 0.1% to about 10% of the tropoelastin promoters, more preferably from about 0.5% to about 5% of tropoelastin promoters, and most preferably from about 0.5% to about 2% of the tropoelastin promoters.

"Collagen promoter," as used herein, refers to compounds that possess the biological activity of enhancing the production of collagen. "Non-retinoid collagen promoters" according to the present invention include all natural or synthetic compounds that are not retinoids, or derived from retinoids, and are capable of enhancing the production of collagen in the human body.

Examples of suitable collagen promoters include, but are not limited to the following: Retinoids including retinol, retinaldehyde, and retinoic acid, extracts of feverfew (*Tanacetum parthenium*), extracts of *Centella asiatica*, and extracts of *Siegesbeckia orientalis*; extracts of soy; collagen-promoting peptides; ursolic acid; and asiaticoside.

*Centella asiatica*, also known as *Violette marronne* on Reunion Island, Gotu Kola or Indian pennywort in India, *Centella repanda* in North America, and Talapetraka in Madagascar, is a polymorphous herb and belongs to the family of Umbelliferae (Apiaceae), particularly to the Hydrocotyle subfamily. It grows wild throughout the tropics and prefers moist and shady regions at an altitude of about 600 to 1200 meters above sea level. *Centella asiatica* has three varieties: Typica, Abyssinica, and Floridana. The herb is known and used for its healing, sedative, analgesic, antidepressant, antiviral and antimicrobial properties. The biological activity of the herb appears to be due to the presence of triterpene molecules in the herb. A suitable extract of *Centella asiatica* is available as TECA from Bayer Consumer HealthCare of Basel, Switzerland.

By "extracts of *Siegesbeckia orientalis*," is meant any of various extracts of the plant *Siegesbeckia orientalis*, including Darutoside available from Sederma (Croda International Group of Edison, N.J.).

Suitable collagen-promoting peptides include the following matrikine peptides, (i.e., a peptide derived from the degradation of extracellular matrix proteins—collagen, elastin, or proteoglycan) including palmitoyl pentapeptides, in particular Pal-Lys-Thr-Thr-Lys-Ser-OH, available as MATRIXYL from Sederma (Croda International Group of Edison, N.J.); GHK copper peptide available as PROCYTE from Photomedex of Montgomeryville, Pa.; Palmitoyl GHK peptide available as Biopoeptide CL from Sederma (Croda International Group of Edison, N.J.); Biomimetic tetrapeptides, such as those available as Chronoline Tri Peptide from Unipex of Québec, Canada; and Palmitoyl tri-peptide, available as Syn-Coll from DSM of Basel, Switzerland.

Ursolic acid is also known as pentacyclic triterpene acid, Prunol, Malol, Urson, betaursolic acid and 3-Beta-Hydroxy-Urs-12-En-28-Oic Acid. It is commercially available for example from Sigma-Aldrich of St. Louis, Mo.

Asiaticoside, also known chemically as: [6-[[3,4-dihydroxy-6-(hydroxymethyl)-5-(3,4,5-trihydroxy-6-methyl-oxan-2-yl)oxyoxan-2-yl]oxymethyl]-3,4,5-trihydroxyoxan-2-yl]10,11-dihydroxy-9-(hydroxymethyl)-1,2,6a,6b,9,12a-hexamethyl-2,3,4,5,6,6a,7,8,8a,10,11,12,13,14b-tetradecahydro-1H-picene-4a-carboxylate) is commercially available for example from Bayer Sante Familiale Division Serdex, 69, Boulevard Victor Hugo 93400 SAINT-OUEN France.

Compositions of the present invention may include a cosmetically effective amount of one or more collagen promoters. The compositions preferably include, on an active basis, from about 0.1% to about 10% of the collagen promoters, more preferably from about 0.5% to about 5% of collagen promoters, and most preferably from about 0.5% to about 2% of the collagen promoters.

The compositions of the present invention may further comprise at least additional skin lightening active agent. Examples of suitable skin lightening active agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, Chamomilla extract, allantoin, opacifiers, talcs and silicas, zinc salts, and the like, and other agents as described in Solano et al. Pigment Cell Res. 19 (550-571) and Ando et al. Int J Mol Sci 11 (2566-2575).

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, Dioscorea Coposita root extract, Saxifraga extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkylresorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin degradation agents include, but are not limited to, peroxides and enzymes such as peroxidases and ligninases. In certain preferred embodiments, the melanin inhibiting agents include a peroxide or a ligninase.

Examples of suitable melanosome transfer inhibiting agents including PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliants include glycolic acid or salicylic acid.

Examples of sunscreens include, but are not limited to, avobenzone (Parsol 1789), bisdisulizole disodium (Neo Heliopan AP), diethylamino hydroxybenzoyl hexyl benzoate (Uvinul A Plus), ecamsule (Mexoryl SX), methyl anthranilate, 4-aminobenzoic acid (PABA), cinoxate, ethylhexyl triazone (Uvinul T 150), homosalate, 4-methylbenzylidene camphor (Parsol 5000), octyl methoxycinnamate (Octinoxate), octyl salicylate (Octisalate), padimate O (Escalol 507), phenylbenzimidazole sulfonic acid (Ensulizole), polysilicone-15 (Parsol SLX), trolamine salicylate, Bemotrizinol (Tinosorb S), benzophenones 1-12, dioxybenzone, drometrizole trisiloxane (Mexoryl XL), iscotrizinol (Uvasorb HEB), octocrylene, oxybenzone (Eusolex 4360), sulisobenzone, bisoctrizole (Tinosorb M), titanium dioxide, zinc oxide, and the like.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfhydryl compounds and their derivatives (e.g., sodium metabisulfite and N-acetyl cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, Portulaca extract, Licochalcone, chalcone, 2,2'-dihydroxy chalcone, Primula extract, propolis, and the like.

The additional cosmetically active agent may be present in a composition in any suitable amount, for example, in an amount of from about 0.0001% to about 20% by weight of the composition, e.g., about 0.001% to about 10% such as about 0.01% to about 5%. In certain preferred embodiments, in an amount of 0.1% to 5% and in other preferred embodiments from 1% to 2%.

Compositions of the present invention may include a cosmetically effective amount of one or more anti-inflammatory compounds. Examples of suitable anti-inflammatory agents include substituted resorcinols, (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), extracts and materials derived from the following: *Phellodendron amurense* Cortex Extract (PCE), Non-Denatured Soy (*Glycine max*), Feverfew (*Tanacetum parthenium*), Ginger (*Zingiber officinale*), Ginko (*Ginkgo biloba*), Madecassoside (*Centella asiatica* extract ingredient), *Cotinus* (*Cotinus coggygria*), Butterbur Extract (*Petasites hybridus*), Goji Berry (*Lycium barbarum*), Milk Thistle Extract (*Silybum marianum*), Honeysuckle (*Lonicera japonica*), Basalm of Peru (*Myroxylon pereirae*), Sage (*Salvia officinalis*), Cranberry Extract (*Vaccinium oxycoccos*), Amaranth Oil (*Amaranthus cruentus*), Pomegranate (*Punica granatum*), Yerbe Mate (*Ilex paraguariensis* Leaf Extract), White Lily Flower Extract (*Lilium candidum*), Olive Leaf Extract (*Olea europaea*), Phloretin (apple extract), Oat Flour (*Aveena sativa*), Lifenol (Hops: *Humulus lupulus*) Extract, Bugrane P (*Ononis spinosa*), Licochalcone (Licorice: *Glycyrrhiza inflate* extract ingredient), Symrelief (Bisabolol and Ginger extract), combinations of two or more thereof, and the like.

In one embodiment, the anti-inflammatory agent is a resorcinol. Particularly suitable substituted resorcinols include 4-hexyl resorcinol and 4-octylresorcinol, particularly 4-hexyl resorcinol. 4-Hexyl resorcinol is commercially available as "SYNOVEA HR" from Sytheon of Lincoln Park, N.J. 4-Octylresorcinol is commercially available from City Chemical LLC of West Haven, Conn.

By "extracts of feverfew," it is meant extracts of the plant "*Tanacetum parthenium*," such as may be produced according to the details set for the in US Patent Application Publication No. 2007/0196523, entitled "PARTHENOLIDE FREE BIOACTIVE INGREDIENTS FROM FEVERFEW (TANACETUM PARTHENIUM) AND PROCESSES FOR THEIR PRODUCTION." (Incorporated by reference herein in their entirety). One particularly suitable feverfew extract is commercially available as about 20% active feverfew, fromlntegrated Botanical Technologies of Ossining, N.Y.

The compositions of the present invention may also include botanical extracts from certain species of the genus *Paulownia*. These extracts and their use in skin compositions including compositions for lightening human skin are disclosed in US Patent Applications 20120045490, 20120045491 and 20120045530 (incorporated by reference herein in their entirety).

A variety of other materials may also be present in the compositions of the present invention. In certain preferred embodiments, the composition comprises one or more topical ingredients selected from the group consisting of: surfactants, chelating agents, emollients, humectants, conditioners, preservatives, opacifiers, fragrances and the like.

What is meant by an emollient is a compound that helps to maintain the soft, smooth, and pliable appearance of the skin (e.g., by remaining on the skin surface or in the stratum corneum to act as a lubricant). Examples of suitable emollients include those found in Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.), and include, but are not limited to, petrolatum, hexyldecyl stearate and plant, nut, and vegetable oils such as macadamia nut oil, rice bran oil, grape seed oil, palm oil, prim rose oil, hydrogenates peanut oil, and avocado oil.

What is meant by a humectant is a compound intended to increase the water content of the top layers of skin (e.g., hygroscopic compounds). Examples of suitable humectants include those found ind Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.) and include, but are not limited to, glycerin, sorbitol or trehalose (e.g., $\alpha,\alpha$-trehalose, $\beta,\beta$-trehalose, $\alpha,\beta$-trehalose) or a salt or ester thereof (e.g., trehalose 6-phosphate).

What is meant by a surfactant is a surface-active agent intended to cleanse or emulsify. Examples of suitable surfactants include those found in Chapter 37, pages 431-450 (Classification of surfactants, by L. Oldenhove de Guertechin) in Handbook of Cosmetic Science and Technology (edited by A. Barel, M. Paye and H. Maibach, Published in 2001 by Marcel Dekker, Inc., New York, N.Y.) and include, but are not limited to anionic surfactants such as sulfates, cationic surfactants such as betaines, amphoteric surfactants such as sodium coco glycinate, noionic surfactants such as alkyl polyglucosides.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the trade name, "Versene 100XL."

Suitable preservatives include, for example, parabens, quaternary ammonium species, phenoxyethanol, benzoates, DMDM hydantoin, organic acids and are present in the composition in an amount, based upon the total weight of the composition, from about 0 to about 1 percent or from about 0.05 percent to about 0.5 percent.

Any of a variety of commercially available pearlescent or opacifying agents are suitable for use in the composition. Examples of suitable pearlescent or opacifying agents include, but are not limited to, mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: $HO\text{-}(JO)_a\text{---}H$, wherein J is an alkylene group having from about 2 to about 3 carbon atoms; and a is 2 or 3; fatty alcohols containing from about 16 to about 22 carbon atoms; fatty esters of the formula: $KCOOCH_2L$, wherein K and L independently contain from about 15 to about 21 carbon atoms; inorganic solids insoluble in the shampoo composition, and mixtures thereof.

Any fragrance compositions suitable for use on skin may be used in the composition according to the present invention.

In certain preferred embodiments, the present invention is in the form of a substrate comprising a composition of the present invention. Any suitable substrate may be used. Examples of suitable substrates and substrate materials are disclosed, for example, in U.S. Pat. No. 7,452,547 and US2009/0241242 which are incorporated herein by reference in their entirety.

In certain preferred embodiments, the substrate is a wipe, glove, or a facial mask. Preferably, such embodiments comprise a water-insoluble substrate as such is defined in the cited references above. For certain embodiments, the water-insoluble substrate may have a size and shape such that it covers the face of a human user to facilitate placing the water-insoluble substrate about the face of the user as a mask substrate. For example, the water-insoluble mask substrate may have openings for a mouth, nose, and/or eyes of the user. Alternatively, the water insoluble substrate may have no such openings. Such a configuration without openings may be useful for embodiments of the invention in which the water-insoluble substrate is intended to be draped over a non-facial expanse of skin or if the water-insoluble substrate is intended to be used as wipe. The water-insoluble substrate may have various shapes, such as an angular shape (e.g., rectangular) or an arcuate shape such as circular or oval. For certain embodiments, the substrate is a glove such as described in U.S. Published Application No 2006/0141014 which is incorporated herein in its entirety. In one embodiment of the invention, the product includes a plurality of water-insoluble substrates of different shapes.

Any suitable method of applying the composition to the skin in need may be used. For example, the composition may be applied directly from a package to the skin in need, by hand to the skin in need, or may be transferred from a substrate such as a wipe or mask, or a combination of two or more thereof. In other embodiments, the composition may be applied via a dropper, tube, roller, spray, and patch or added to a bath or otherwise to water to be applied to the skin, and the like. The composition may be applied in a variety of manners or forms, including, without limitation, as a leave-on cream, mask, and/or serum.

In further additional embodiments, the methods of the present invention comprise applying at least two different compositions or products comprising the cell culture extracts of *Earliella scabrosa* to the skin. For example, the methods may comprise applying a first composition comprising the extracts of *Earliella scabrosa* to skin in need of improving skin barrier function and improving skin hydration and moisturization, followed by applying a second composition comprising the cell culture extracts of *Earliella scabrosa* that is different from the first composition, to the skin in need of treatment. In certain preferred embodiments, the first and second composition may be independently selected from the group consisting of lotions, cleansers, masks, wipes, creams, serums, gels, and the like. In certain preferred embodiments, at least one of the first and second compositions is a cleanser, lotion, cream, cosmetic film, essence, or serum, and the other is a facial mask or wipe. In certain other preferred embodiments, at least one of the first and second compositions is a cleanser and the other is a lotion or cream.

Method of Culturing

Another aspect of the current invention is a method of optimizing the culturing of the fungi. Applicants have conducted a series of experiments to modify the culture media, the pH and the agitation to produce a cell culture extract with unexpectedly improved skin lightening properties.

As used herein "modifying the culture media' means changing the type and amounts of the ingredients used in the culture. For example, the source of ammonia used in the cell culture can be ammonium nitrate, rice bran, wheat bran, yeast extract or mixtures thereof. Organic nitrogen sources such as beef extract, tryptone, peptone, soytone, wheat straw and inorganic nitrogen source such as ammonium tartrate, ammonium sulfate, ammonium chloride or mixtures thereof can also be used as ammonia sources in the cell culturing process. The amount of nitrogen source in the culture media can be from about 0.1 g/L to about 25 g/L or from about 0.2 to about 20 g/L or from about 5 g/L to about 20 g/L. The amount of carbon source in the media can also be modified. The amount of carbon can range from about 2 to about 20 g/L or from about 5 to about 15 g/l or from about 5 to about 10 g/L. The source of carbon can be selected from the group consisting of glucose or dextrose or mixtures thereof.

The pH of the culture media can be modified by adding a buffering system. One system is a combination of sodium hydroxide and hydrochloric acid. Other buffering systems known in the art can be used to modify the pH.

The method of culturing the media can be modified by changing the agitation. An incubator shaker known to those skilled in the art can be used to agitate the media during the culturing. The shaker can be set at about a range of about 100 to about 200 rpm.

An additional way to modify the culture media is by adding an inducer. An inducer is a substance that enhances the melanin degrading enzyme production of the fungus being cultured. Examples of inducers include synthetic melanin, sepia melanin, veratryl alcohol, lignin, organic compounds that contain one or more benzene or equivalent heterocyclic rings, benzyl alcohol, cinnamic acid, guaiacol, methyl salicylate, benzenediol, benzoquinone, Gallic acid, salicylic acid, eugenol, caffeic acid, xylenol. or mixtures thereof. The amount of inducer added to the media composition can range from about 10 mg/L to about 2000 mg/L or from about 30 mg/L to about 1000 mg/L or from about 200 mg/L to about 400 mg/L or from about 245 mg/L to about 350 mg/L.

While the foregoing description and drawings represent exemplary embodiments of the present invention, it will be understood that various additions, modifications and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description. It will be appreciated that in the claims, the term "comprises/comprising" does not exclude the presence of other elements or steps. In addition, singular references do not exclude a plurality. The terms "a", "an", "first", "second", etc., do not preclude a plurality.

EXAMPLES

*E. scabrosa* stock culture was grown and maintained on Potato Dextrose Agar (PDA), pH 6.0. From the stock culture, small blocks of agar containing fungal mycelium were cut using a cork borer with a diameter of 0.7 cm, which were then subcultured on solid agar for subsequent studies. All culture plates were incubated at 30° C. for 3 to 5 days until fungal growth was observed. For sub-culturing in liquid medium broth, stock culture agar containing fungal mycelium was first cut into 1.5 cm×3.0 cm then further cut into smaller pieces before inoculated into 50 ml of liquid medium broth and incubated at 30° C. for 7 to 9 days. *E. scabrosa* culture filtrate was obtained from cultured medium broth for subsequent studies described in the examples below.

Example 1: Melanin Agar Screening

*Earliella scabrosa* MY993 was cultured on a melanin agar plate and incubated for 9 days. The melanin agar composition used is listed in Table 1.

TABLE 1

| Composition | Weight (g/L) | Supplier | Cat. No. |
| --- | --- | --- | --- |
| Glucose | 10 | Carlo Erba | 346971 |
| Malt extract | 2 | Difco | 218630 |
| Magnesium sulfate heptahydrate | 4 | Carlo Erba | 10034.99.8 |
| Potassium dihydrogen phosphate | 1 | Carlo Erba | 471687 |
| Iron II sulfate | 0.01 | Carlo Erba | 451926 |
| Zinc sulfate | 0.005 | Carlo Erba | 494907 |
| Synthetic melanin | 0.2 | Sigma Aldrich | M8631 |
| Agar | 15 | Difco | 281230 |

Melanin agar medium was prepared from the composition listed in Table 1. All ingredients were added to 1 L of water and was autoclaved at 121° C. for 15 mins. After autoclave, the agar medium was dispensed into petri dishes (20 ml per plate) and left to solidify.

From fungi stock cultures, small blocks of agar containing the fungal mycelium were cut using a cork borer with a diameter of 0.7 cm, which were then subcultured by placing the fungal block on the center of a fresh agar plate and incubated at 30° C. for 9 days.

Strain number MY993 (*Earliella scabrosa*) was observed to decolorize melanin in agar over the nine days with some decolorization showing at 5 days and increasing decolorization at 7 and 9 days. Photographs of the agar plates at days 3, 5, 7 and 9 are shown in FIG. 1.

Figure 2:
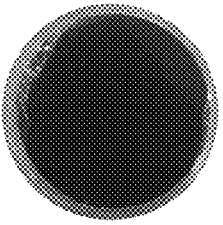
FIG. 2 is a photograph of a series of melanin agar plates cultured with white rot fungi strains that did not decolorize melanin.

In contrast, other white rot fungi strains such as *Ganoderma* sp. (TDR 0003), *Lentinus* sp. (TDR 0008) and *Amauroderma* sp. (TRD 0023) were cultured on the same media and did not show signs of any deolorization of the melanin over 9 days. The agar plates for the controls at days 3, 5, 7 and 9 are shown in FIG. 2.

Example 2: Activity of *Earliella scabrosa* in a Conditioned Broth Media

*Earliella scabrosa* was cultured in a liquid media broth using one liter of water with the composition listed in TABLE 2.

TABLE 2

| Composition | Weight | Supplier | Cat. No. |
|---|---|---|---|
| Glucose | 10 g/L | Carlo Erba | 346971 |
| Yeast extract | 0.2 g/L | Difco | 212750 |
| Ammonium tartrate dibasic | 3 g/L | Fluka | 09985 |
| Tween 80 | 1 g/L | Merck | 8221870500 |
| Potassium dihydrogen phosphate | 0.2 g/L | Carlo Erba | 471687 |
| Calcium Chloride dihydrate | 0.146 g/L | BDH | 100704Y |
| Magnesium sulfate heptahydrate | 0.05 g/L | Carlo Erba | 10034.99.8 |
| Zinc sulfate heptahydrate | 42.5 mg/L | Carlo Erba | 494907 |
| Manganese sulfate monohydrate | 3.38 mg/L | Carlo Erba | 10034.96.5 |
| Cobalt II chloride hexahydrate | 7 mg/L | Carlo Erba | 439355 |
| Copper sulfate heptahydrate | 7 mg/L | BDH | 100915R |
| Iron III chloride | 0.54 mg/L | Merck | 8.03945.0500 |
| Sodium chloride | 0.9 mg/L | Carlo Erba | 479687 |
| Synthetic melanin | 200 mg/L | Sigma Aldrich | M8631 |

From *E. scabrosa* stock culture, small blocks of agar containing the fungal mycelium was first cut into 1.5 cm×3.0 cm sections then further cut into smaller pieces before inoculated into 50 ml of medium broth and incubated at 30° C. for 9 days using an incubator shaker with agitation speed of 100 rpm. After centrifugation, the supernatant was then filtered through a 0.22 um filter prior to testing in a melanin-degrading activity assay. *E. scabrosa* culture filtrate was harvested at Day 3, 5, 7 and 9 by centrifugation at 12,396 g for 5 mins.

Example 3: Melanin Degrading Assay

Melanin degrading assay was conducted in 96-well plate where each reaction mix (total volume 250 μL) comprised of 904, synthetic melanin (250 mg/L, pH 6.0), 1104, distilled water and 504, *E. scabrosa* culture filtrate. Reaction mix was then incubated at 37° C. for 1 hour and measured at the absorbance of 540 nm with a spectrophotometer. One unit of melanin (U/ml) degrading enzyme activity was defined as the amount of enzyme that decreased the absorbance at 540 nm by 0.001 for 1 hour at 37° C.

Selected strains of *E. scabrosa* displayed high melanin-degrading activities from Day 3, 5, 7 and 9 culture filtrate, and activity peaked at Day 7 as shown in Table 3.

TABLE 3

| Earliella | Melanin-degrading activity (U/ml) | | | |
|---|---|---|---|---|
| scabrosa | Day 3 | Day 5 | Day 7 | Day 9 |
| MY993 | 1364.35 | 1686.60 | 1706.63 | 1500.15 |
| MY261 | 606.44 | 1096.51 | 1297.84 | 1236.30 |

Example 4: Comparison of Melanin Degrading Activity to Laccase Enzyme

White rot fungi are known to secrete laccase enzyme. The laccase activity of selected strains of *E. scabrosa* were measured. Laccase activity was measured using the 2,2-azino-bis-(3-ethylbenzothiazoline-6-sulphonic acid) (ABTS) assay and was calculated using the following equation:

$$\text{Activity} = (\Delta E \times DF \times Vt)/(\Delta t \times Vs \times d \times \varepsilon 420)$$

The pH of the 50 μL *E. scabrosa* culture filtrate (Vs) was adjusted to 5.5 with 150 μL of 80 mM sodium acetic acid buffer, pH 5.5. All samples were diluted to appropriate dilution (dilution factor=DF). After the addition of 50 μL of 5 mM ABTS solution, the change of absorbance ($\Delta E$) was measured for 5 minutes ($\Delta t$) at 420 nm and 37° C. Laccase activity was calculated using an extinction coefficient of $\varepsilon_{420} = 0.04321$ L $\mu mol^{-1}$ $cm^{-1}$, a layer height d=0.63 cm and a total liquid volume of Vt=250 μL. The assay was done in spectrophotometer. Laccase enzyme activity (U) is defined as the amount of enzyme catalyzing the oxidation of 1 μmol ABTS per minute at 37° C. and pH 5.5.

As shown in TABLE 4, it was found that laccase activity does not correlate to melanin-degrading activity. This suggests that laccase is not the primary driver for the melanin degradation activity of *Earliella scabrosa*.

TABLE 4

| | | Day 7 culture filtrate | |
|---|---|---|---|
| strains | | Melanin-degrading activity | Laccase activity |
| MY993 | Earliella | 1706.63 | 1348.25 |
| MY 261 | scabrosa | 1297.84 | 105.70 |

Examples 5 and 5A: Optimization of Growth Conditions

Two sizes of cell cultures were compared to examine the effect of changing several of the components of the culture. The components of two one liter liquid broth cultures, before and after optimization, are shown in TABLE 5. Then two separate before and after experiments were done to test the melanin degrading activity of the before and after broth compositions. Example 5 is a 50 ml cell culture and Example 5A is five liter cell culture. Both Examples 5 and 5A used the same ingredients in the same proportions for both before and after optimization. The optimized formula included removal of yeast extract, addition of wheat bran and veratryl alcohol and increasing the pH to 6 and setting the fermentation aeration rate from 0.6 vvm to 1.0 vvm. Each culture was used to grow E. scabrosa MY993. After centrifugation, the supernatant was then filtered through 0.22 μm filter prior to testing in the melanin-degrading activity assay used in Example 3.

The melanin-degrading activity of E. scabrosa extract was shown to increase by 23% after optimization of growth conditions in lab scale of 50 mL and 778% after a 5 liter batch of optimized media as shown in TABLE 6.

TABLE 5

| Growth conditions | | Before optimization | After optimization |
|---|---|---|---|
| Medium composition | Glucose | 10 g/L | 10 g/L |
| | Ammonium tartrate dibasic | 3 g/L | 3 g/L |
| | Tween 80 | 1 g/L | 1 g/L |
| | Potassium dihydrogen phosphate | 0.2 g/L | 0.2 g/L |
| | Calcium Chloride dehydrate | 0.146 g/L | 0.146 g/L |
| | Magnesium sulfate heptahydrate | 0.05 g/L | 0.05 g/L |
| | Zinc sulfate heptahydrate | 42.5 mg/L | 42.5 mg/L |
| | Manganese sulfate monohydrate | 3.38 mg/L | 3.38 mg/L |
| | Cobalt II chloride hexahydrate | 7 mg/L | 7 mg/L |
| | Copper sulfate heptahydrate | 7 mg/L | 7 mg/L |
| | Iron III chloride | 0.54 mg/L | 0.54 mg/L |
| | Sodium chloride | 0.9 mg/L | 0.9 mg/L |
| | Yeast extract | 0.2 g/L | — |
| | Wheat bran | — | 10 g/L |
| | Synthetic melanin | 200 mg/L | — |
| | Veratryl alcohol | — | 0.245 g/L |
| | Distilled water | 1 L | 1 L |
| | pH | 5.5 | 6 |
| Culture agitation speed (rpm) | | 100 | 100 |

TABLE 6

| | Before optimize | After optimize | % increase |
|---|---|---|---|
| Melanin-degrading activity of E. scabrosa MY993 Example 5 (50 ml batch) | 1706.63 U/ml | 2098.48 U/ml | 23 |
| Melanin-degrading activity of E. scabrosa MY993 Example 5A (5 liter batch) | 1706.63 U/ml | 14986 U/ml | 778.0 |

Example 6: Optimization of Growth Conditions—Inducer

The liquid broth media was modified by including an inducer. An inducer is added to a broth media of a high titer promoter to enhance the melanin-degrading enzyme production from E. scabrosa.

The ingredients used in the liquid media are listed in TABLE 7.

TABLE 7

| Composition | Weight | Supplier | Cat. No. |
|---|---|---|---|
| Glucose | 10 g/L | Carlo Erba | 346971 |
| Yeast extract | 0.2 g/L | Difco | 212750 |
| Ammonium tartrate dibasic | 3 g/L | Fluka | 09985 |
| Tween 80 | 1 g/L | Merck | 8221870500 |
| Potassium dihydrogen phosphate | 0.2 g/L | Carlo Erba | 471687 |
| Calcium Chloride dehydrate | 0.146 g/L | BDH | 100704Y |
| Magnesium sulfate heptahydrate | 0.05 g/L | Carlo Erba | 10034.99.8 |
| Zinc sulfate heptahydrate | 42.5 mg/L | Carlo Erba | 494907 |
| Manganese sulfate monohydrate | 3.38 mg/L | Carlo Erba | 10034.96.5 |
| Cobalt II chloride hexahydrate | 7 mg/L | Carlo Erba | 439355 |
| Copper sulfate heptahydrate | 7 mg/L | BDH | 100915R |
| Iron III chloride | 0.54 mg/L | Merck | 8.03945.0500 |
| Sodium chloride | 0.9 mg/L | Carlo Erba | 479687 |

Separate broths were made using the formula in TABLE 7 using one liter of water and the following inducers were added as shown in TABLE 8.

TABLE 8

| Inducer | Weight (mg/L) | Supplier | Cat. No. |
|---|---|---|---|
| Synthetic melanin | 200 | Sigma Aldrich | M8631 |
| Sepia melanin | 200 | Sigma Aldrich | M2649 |
| 3,4-Dimethoxybenzyl alcohol (Veratryl alcohol) | 35, 175, 245 and 350 | Sigma Aldrich | D133000 |
| Lignin | 200, 400, 1000 and 2000 | Sigma Aldrich | 471003 |

E. scabrosa MY993 was grown in medium supplemented with the different inducers at the various concentrations shown in TABLE 8 and incubated at 30° C. with agitation speed of 100 rpm using an incubator shaker.

From E. scabrosa MY993 stock culture, small blocks of agar containing the fungal mycelium was first cut into 1.5 cm×3.0 cm then further cut into smaller pieces before inoculated into 50 ml of medium broth supplemented with the different inducers at the various concentrations shown in the table and incubated at 30° C. with agitation speed of 100 rpm and incubated at 30° C. for 9 days using an incubator shaker with agitation speed of 100 rpm. E. scabrosa culture filtrate was harvested at Day 1, 3, 5 and 7 by centrifugation at 12,396 g, 5 mins. After centrifugation, the supernatant was then filtered through 0.22 μm filter prior to testing in the melanin-degrading activity assay used in Example 3.

The results are summarized in TABLE 9. 245 mg/L of veratryl alcohol was shown to be the best inducer to enhance melanin-degrading enzyme production in E. scabrosa MY993 extract at the Day 7 culture filtrate.

TABLE 9 (Melanin-degrading activity of *E. scabrosa* MY993 Day 1, 3, 5 and 7 culture filtrate.

TABLE 9

| Inducer | Conc (mg/L) | Melanin-degrading activity (U/ml) | | | |
|---|---|---|---|---|---|
| | | Day 1 | Day 3 | Day 5 | Day 7 |
| Synthetic melanin | 200 | 288.85 | 1022.90 | 1331.30 | 1491.73 |
| Sepia melanin | 200 | 130.14 | 380.91 | 950.43 | 1506.23 |
| Veratryl alcohol | 35 | 215.73 | 313.19 | 793.75 | 1332.00 |
| | 175 | 195.65 | 394.28 | 941.80 | 1472.68 |
| | 245 | 191.21 | 345.43 | 1082.43 | 1604.49 |
| | 350 | 0.00 | 1023.26 | 1292.12 | 1553.47 |
| Purified lignin | 200 | 192.65 | 218.47 | 325.66 | 923.47 |
| | 400 | 195.45 | 164.95 | 495.71 | 999.99 |
| | 1000 | 258.97 | 161.37 | 694.89 | 1029.81 |
| | 1400 | 276.70 | 155.96 | 768.44 | 1104.36 |

Example 7: Optimization of Nitrogen Source and pH

One liter liquid broth cultures were made to test effect of the source of nitrogen and pH on the melanin degrading activity of the cell culture extract. The broth used is listed in TABLE 10.

TABLE 10

| Composition | Weight | Supplier | Cat. No. |
|---|---|---|---|
| Glucose | 10 g/L | Carlo Erba | 346971 |
| Ammonium tartrate dibasic | 3 g/L | Fluka | 09985 |
| Tween 80 | 1 g/L | Merck | 8221870500 |
| Potassium dihydrogen phosphate | 0.2 g/L | Carlo Erba | 471687 |
| Calcium Chloride dehydrate | 0.146 g/L | BDH | 100704Y |
| Magnesium sulfate heptahydrate | 0.05 g/L | Carlo Erba | 10034.99.8 |
| Zinc sulfate heptahydrate | 42.5 mg/L | Carlo Erba | 494907 |
| Manganese sulfate monohydrate | 3.38 mg/L | Carlo Erba | 10034.96.5 |
| Cobalt II chloride hexahydrate | 7 mg/L | Carlo Erba | 439355 |
| Copper sulfate heptahydrate | 7 mg/L | BDH | 100915R |
| Iron III chloride | 0.54 mg/L | Merck | 8.03945.0500 |
| Sodium chloride | 0.9 mg/L | Carlo Erba | 479687 |

The nitrogen sources are listed in TABLE 11.

TABLE 11

| Nitrogen source | Weight (g/L) | Supplier | Cat. No. |
|---|---|---|---|
| Rice bran | 0.2 | Narapimol rice mill | — |
| Wheat bran | 0.2 | JFK Feed | — |
| Ammonium nitrate | 0.2 | Fluka | 09700 |
| Yeast extract | 0.2 | Difco | 212750 |

*E. scabrosa* MY993 was grown in separate media supplemented with the nitrogen sources and at different pH of 4 to 7 and incubated at 30° C. with agitation speed of 100 rpm with an incubation shaker. *E. scabrosa* MY993 culture filtrate from different conditions were harvested at Day 1, 3, 5 and 7. The culture filtrate was then filtered through 0.22 µm filter prior testing in melanin-degrading activity assay which is described in Example 3.

Rice bran and wheat bran were shown to be better enhancers than ammonium nitrate. With wheat bran as a best candidate to replace yeast extract (TABLE 12) for enhancing melanin-degrading enzyme production. Cultures using rice bran and wheat bran were made at pH of 4, 5, 5.5, 6 and 7. pH adjustment was done by using sodium hydroxide and hydrochloric acid. The results are shown in TABLE 13. At Day 7, both rice bran and wheat bran produced elevated melanin degrading activity from a pH of 5-6.

TABLE 12: Melanin-degrading activity of *E. scabrosa* MY993 Day 1, 3, 5 and 7 culture filtrate harvested from media supplemented (pH 5.5) with different nitrogen source

TABLE 12

| Nitrogen source | Melanin-degrading activity | | | |
|---|---|---|---|---|
| | Day 1 | Day 3 | Day 5 | Day 7 |
| Rice bran | 427.42 | 1443.18 | 1312.18 | 1309.19 |
| Wheat bran | 423.08 | 1298.88 | 1450.3 | 1515.21 |
| Ammonium nitrate | 470.66 | 1087.96 | 1015.62 | 1066.41 |
| Yeast extract | 455.14 | 1423.28 | 1535.86 | 1580.45 |

TABLE 13: Melanin-degrading activity of *E. scabrosa* MY993 Day 1, 3, 5 and 7 culture filtrate harvested from media supplemented with rice bran and wheat bran at a different pH.

TABLE 13

| Nitrogen source | pH | Melanin-degrading activity | | | |
|---|---|---|---|---|---|
| | | Day 1 | Day 3 | Day 5 | Day 7 |
| Wheat bran | 4.0 | 304.81 | 542.37 | 665.06 | 504.90 |
| | 5.0 | 362.38 | 998.39 | 1100.88 | 945.29 |
| | 5.5 | 289.71 | 1096.00 | 1417.52 | 1160.91 |
| | 6.0 | 163.64 | 960.69 | 1370.03 | 1573.93 |
| | 7.0 | 29.98 | 388.91 | 845.84 | 549.80 |
| Rice bran | 4.0 | 224.38 | 434.19 | 442.64 | 254.54 |
| | 5.0 | 247.00 | 782.71 | 1286.51 | 1292.68 |
| | 5.5 | 208.96 | 937.31 | 1223.63 | 1140.48 |
| | 6.0 | 214.95 | 906.50 | 1344.60 | 1399.14 |
| | 7.0 | 2.51 | 393.85 | 849.33 | 707.44 |

Example 8: Optimization of Agitation Speed of Culture

*E. scabrosa* MY993 was grown in medium supplemented with wheat bran at pH 6.0 and incubated at 30° C. with agitation speed of 100 rpm, 200 rpm with an incubator shaker and static condition.

*E. scabrosa* MY993 culture filtrate from different conditions were harvested at Day 1, 3, 5 and 7. The cultured filtrate was then filtered through a 0.22 um filter prior testing in melanin-degrading activity assay using the assay described in Example 2 above.

Agitation speed of 100 rpm was observed to be the optimum condition for enhancing Melanin-degrading enzyme production from *E. scabrosa* (Table 14).

TABLE 14: Melanin-degrading activity of *E. scabrosa* Day 1, 3, 5 and 7 culture filtrate harvested from different agitation conditions.

TABLE 14

| Agitation condition | Melanin-degrading activity | | | |
| --- | --- | --- | --- | --- |
| | Day 1 | Day 3 | Day 5 | Day 7 |
| Static condition | 364.22 | 316.14 | 881.30 | 652.05 |
| 100 rpm | 163.64 | 960.69 | 1370.03 | 1573.93 |
| 200 rpm | 250.10 | 304.24 | 1405.52 | 1419.30 |

Example 9: Optimization of Glucose and Wheat Bran Concentration

E. scabrosa MY993 was grown in medium supplemented with different wheat bran concentration of 0.2, 1, 2, 5, 10 and 20 g/L and different glucose concentration of 2.5, 5 and 10 g/L. Cultures were incubated at 30° C. with agitation speed of 100 rpm with an incubator shaker. E. scabrosa culture filtrate from different conditions were harvested at Day 1, 3, 5 and 7. The culture filtrate was then filtered through 0.22 um filter prior testing in the melanin-degrading activity assay described above.

10 g/L glucose was shown to be the optimum condition for enhancing melanin-degrading enzyme production from E. scabrosa MY993 (Table 15).

20 g/L wheat bran was shown to be the optimum condition for enhancing melanin-degrading enzyme production from E. scabrosa MY993 (Table 15). At 20 g/L concentration, the cultures tend to overgrow thus not suitable to be used in scale up fermentation, instead 10 g/L wheat bran was chosen as the final concentration for large scale (5 L) production.

TABLE 15: Melanin-degrading activity of E. scabrosa MY993 Day 1, 3, 5 and 7 culture filtrate harvested from media supplemented with different glucose concentrations.

TABLE 15

| Glucose concentration | Melanin-degrading activity | | | |
| --- | --- | --- | --- | --- |
| (g/L) | Day 1 | Day 3 | Day 5 | Day 7 |
| 2.5 | 222.91 | 1027.04 | 899.58 | 1836.59 |
| 5 | 353.06 | 1175.72 | 1068.20 | 2450.79 |
| 10 | 139.25 | 1397.22 | 1332.10 | 2659.82 |

TABLE 16: Melanin-degrading activity of E. scabrosa MY993 Day 1, 3, 5 and 7 culture filtrate harvested from media supplemented with different wheat bran concentrations.

TABLE 16

| Wheat bran concentration | Melanin-degrading activity | | | |
| --- | --- | --- | --- | --- |
| (g/L) | Day 1 | Day 3 | Day 5 | Day 7 |
| 0.2 | 540.60 | 1573.71 | 1905.51 | 1628.88 |
| 1 | 507.47 | 1684.74 | 1818.92 | 1497.51 |
| 2 | 599.54 | 1817.28 | 1960.74 | 1549.72 |
| 5 | 542.02 | 1801.26 | 2203.71 | 1687.98 |
| 10 | 494.31 | 1709.39 | 2062.58 | 2098.48 |
| 20 | 217.67 | 1230.85 | 2545.97 | 2400.62 |

Example 10: Melanoderm Testing

Commercially available pigmented epidermal equivalent tissues or MelanoDerm™ Model from MatTek Corp. were used for the following tests. The MelanoDerm™ Model consists of normal, human-derived epidermal keratinocytes (NHEK) and melanocytes (NHM) which have been cultured to form a multilayered, highly differentiated model of the human epidermis. Specifically, MEL-300-B tissues, each 9 mm in diameter were used in the following tests. E. scabrosa culture filtrate were applied topically to the MelanoDerm™ model daily and the experiment lasted for 8 days. Measurement was taken on day 9. The macroscopic and microscopic visual tissue darkening end points were measured by taking pictures with a digital camera. The Degree of Lightness for each tissue (L-Value) was measured using a spectrophotometer (Konica Minolta CM-2600d). The ΔL (degree of lightness as compared to control) for each test sample is calculated as per following formula: ΔL=L-value of treated sample—L-value of control sample.

Figure 3:
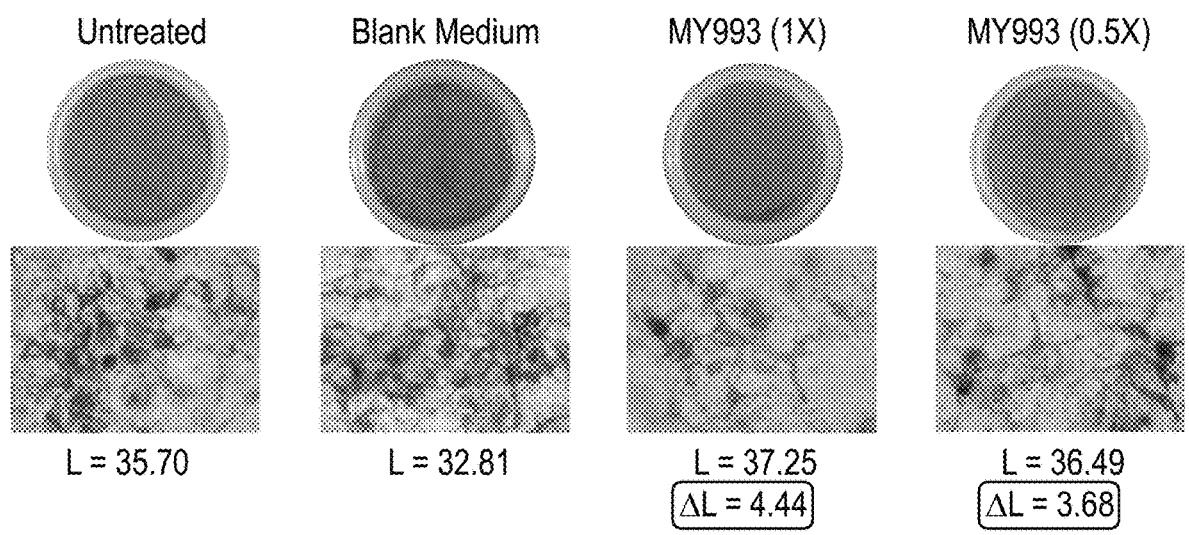
FIG. 3 is a photograph of Melanoderm 3D skin equivalent models showing that *Earliella scabrosa* culture extract (MY993) reduced pigmentation

Four samples were tested—untreated (the skin model with nothing added), blank medium (a cell culture media with no fungus), MY993 (1×—undiluted) and MY993 (0.5×—diluted half strength with cell culture media.). The results are shown in Table 17 and photographs of the media agar plates and the Meloderm model are shown in FIG. 3. Both the ΔL and the Meloderm model show that extracts according to the present invention reduced pigmentation. Therefore, the cell culture extracts of E. scabrosa would be expected to provide skin lightening benefits when applied to the skin.

TABLE 17

| Sample | L | ΔL |
| --- | --- | --- |
| Blank Media | 32.81 | |
| Untreated | 35.7 | — |
| MY993 (1x) | 37.25 | 4.44 |
| MY993 (0.5x) | 36.49 | 3.68 |

Example 11

A skin care composition according to the invention is prepared using the ingredients shown in Table 18.

TABLE 18

| Name | INCI Name | % weight |
| --- | --- | --- |
| Deionized Water | Water | 74.34 |
| Natrosol 250 HHR | Hydroxyethylcellulose | 0.50 |
| Citric Acid | Citric Acid | 0.06 |
| Cell Culture Extract of Earliella scabrosa | | 3.0 |
| Savonol 82 | Mineral Oil | 3.00 |
| Dow Corning 345 Fluid | Cyclopentasiloxane | 2.50 |
| Dow Corning CB 9111 | Cyclopentasiloxane/Dimethicone | 2.00 |
| Dow Corning AP 8087 | Bis-Hydroxy/Methoxy Amodimethicone | 1.00 |
| Genamin BTLF | Behentrimonium Chloride | 3.0 |
| Tego Amid S18 | Stearamidopropyl Dimethylamine | 1.0 |
| Brij 721 | Steareth-21 | 0.5 |
| Lanette C18 98-100 MY | Stearyl Alcohol | 4.5 |
| Glycerin | Glycerin | 6.00 |
| Benzyl Alcohol | Benzyl Alcohol | 0.60 |

The composition shown in Table 18 is prepared as follows: water is added to a process vessel. Mixing begins and hydroxyethylcellulose is added and mixing continues until the hydroxyethylcellulose dissolves. Heat is applied and mixing continues until the temperature reaches 85° C. Glycerin is added while continuing the mixing and maintaining the temperature at 85° C. GENAMIN BTLF and Tego Amid S18 are added, as is Brij 721 and Lanette C18 98-100 MY, Savonol 82, and Dow Corning AP 8087. The composition is mixed at 85° C. for another 10-15 minutes. The composition is then removed from heat and continued to mix and cooled at 40° C.

What is claimed is:

1. A method of lightening the skin comprising applying to human skin in need of lightening a composition including a cosmetically acceptable carrier and a cell culture extract of *Earliella scabrosa* produced from liquid cell culture, wherein the liquid cell culture comprises 3,4-dimethoxybenzyl alcohol present in an amount from about 245 mg/ml to about 350 mg/ml, and wherein the cell culture extract of *Earliella scabrosa* is present in the composition in an amount of from about 0.0001% to about 40% by weight.

2. The method of lightening the skin according to claim 1, wherein said human skin in need of skin lightening is selected from the group consisting of skin darkened by UV, skin with uneven skin tone, skin having one or more pigmented spots, melanin spots, age spots, sun spots, senile lentigos, freckles, lentigos simplex, pigmented solar keratosis, seborrhoeic keratosis, melasma, acne marks, and combinations of two or more thereof.

3. The method of claim 2, wherein said human skin in need of skin lightening treatment is selected from the group consisting of skin having one or more pigmented spots, melanin spots, age spots, sun spots, freckles, acne marks, and combinations of two or more thereof.

4. The method of claim 1, wherein said composition comprises from about 0.01% to about 25% by weight of the cell culture extract of *Earliella scabrosa*.

5. The method of claim 4, wherein said composition comprises from about 0.1% to about 10% by weight of the cell culture extract of *Earliella scabrosa*.

6. The method of claim 1, wherein said composition is in the form of a solution, suspension, lotion, cream, serum, gel, stick, spray, ointment, liquid wash, soap bar, shampoo, hair conditioner, paste, foam, powder, mousse, shaving cream, hydrogel, or film-forming product.

7. The method of claim 1, wherein said applying step comprises transferring said composition from a substrate to the skin.

8. The method of claim 7, wherein said substrate comprises a wipe or facial mask.

9. The method of claim 1, wherein the applying step comprises applying a composition comprising a cell culture extract of *Earliella scabrosa* and an additional skin lightening active agent to the skin.

10. The method of claim 9, wherein said applying step further comprises transferring said composition from a substrate to the skin.

11. The method of claim 10, wherein said substrate comprises a wipe or facial mask.

12. The method of claim 1, further comprising the steps of applying to skin in need of skin lightening a composition comprising a cell culture extract of *Earliella scabrosa* once or twice daily.

13. The method of claim 1, wherein said method comprises applying two or more different compositions comprising a cell culture extract of *Earliella scabrosa* to the skin in need of skin lightening.

14. The method of claim 13, wherein said two or more different compositions comprising a cell culture extract of *Earliella scabrosa* are independently selected from the group consisting of lotions, cleansers, masks, essence, wipes, creams, serums, and gels.

15. The method of claim 14, wherein one of said two or more different compositions is a cleanser and another of said two or more different compositions is a lotion or cream.

16. The method of claim 1, wherein the cell culture extract has a melanin degrading activity of from about 500 to about 2000 U/ml.

17. The method of claim 16, wherein the cell culture extract has a melanin degrading activity of from about 600 to about 1800 U/ml.

18. The method of claim 17, wherein the cell culture extract has a melanin degrading activity of from about 1000 to about 1800 U/ml.

19. A skin care composition comprising a cosmetically acceptable carrier and a cell culture extract of *Earliella scabrosa* produced from liquid cell culture, wherein the liquid cell culture comprises 3,4-dimethoxybenzyl alcohol present in an amount from about 245 mg/ml to about 350 mg/ml, and wherein the cell culture extract of *Earliella scabrosa* is present in the composition in an amount of from about 0.0001% to about 40% by weight.

20. The skin care composition of claim 19, wherein said composition comprises from about 0.01% to about 25% by weight of the cell culture extract of *Earliella scabrosa*.

21. The skin care composition of claim 20, wherein said composition comprises from about 0.1% to about 10% by weight of the cell culture extract of *Earliella scabrosa*.

22. The skin care composition of claim 19, further comprising a second skin lightening agent.

23. The skin care composition of claim 19, wherein the skin care composition is in a form selected from the group consisting of a solution, suspension, lotion, cream, serum, essence, gel, toner, stick, spray, ointment, liquid wash, paste, foam, mousse, powder, shaving cream, wipe, patch, strip, hydrogel, film-forming product, facial masks and skin mask.

24. The skin care composition of claim 19, wherein the cell culture extract has a melanin degrading activity of from about 500 to about 2000 U/ml.

25. The skin care composition of claim 24, wherein the cell culture extract has a melanin degrading activity of from about 600 to about 1800 U/ml.

26. The skin care composition of claim 25, herein the cell culture extract has a melanin degrading activity of from about 1000 to about 1800 U/ml.

27. The skin care composition of claim 22, wherein the second skin lightening agent is selected from the group consisting of tyrosinase inhibitors, melanin-degradation agents, PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, Chamomilla extract, allantoin, opacifiers, talcs, silicas, zinc salts and mixtures thereof.

* * * * *